US011273190B2

(12) United States Patent
Rigdon et al.

(10) Patent No.: US 11,273,190 B2
(45) Date of Patent: Mar. 15, 2022

(54) COMPOSITION OF HEAT-KILLED YEAST AND TAURINE OR A PHYTOMEDICINE FOR THE TREATMENT OF CHRONIC INFLAMMATION

(71) Applicants: Kenda Rigdon, Hoover, AL (US); Frank Brady Rigdon, Hoover, AL (US)

(72) Inventors: Kenda Rigdon, Hoover, AL (US); Frank Brady Rigdon, Hoover, AL (US)

(*) Notice: Subject to any disclaimer, the term of this patent is extended or adjusted under 35 U.S.C. 154(b) by 91 days.

(21) Appl. No.: 16/403,748

(22) Filed: May 6, 2019

(65) Prior Publication Data

US 2020/0353024 A1 Nov. 12, 2020

(51) Int. Cl.
| | |
|---|---|
| A61K 36/06 | (2006.01) |
| A61K 31/145 | (2006.01) |
| A61K 9/14 | (2006.01) |
| A23L 33/145 | (2016.01) |
| A61K 36/22 | (2006.01) |
| A61K 47/36 | (2006.01) |
| A23L 33/105 | (2016.01) |
| A61K 9/00 | (2006.01) |

(52) U.S. Cl.
CPC ............ *A61K 36/06* (2013.01); *A23L 33/105* (2016.08); *A23L 33/145* (2016.08); *A61K 9/0034* (2013.01); *A61K 9/0053* (2013.01); *A61K 9/148* (2013.01); *A61K 31/145* (2013.01); *A61K 36/22* (2013.01); *A61K 47/36* (2013.01)

(58) Field of Classification Search
CPC ...... A61K 36/06; A23L 33/145; A23L 33/105
See application file for complete search history.

(56) References Cited

U.S. PATENT DOCUMENTS

| 7,648,698 B2 | 1/2010 | Braun | |
| 8,460,919 B2* | 6/2013 | Selitrennikoff | .... A61K 39/0002 435/255.1 |

FOREIGN PATENT DOCUMENTS

| WO | 2005/093049 A1 | 10/2005 |
| WO | 2010/032139 A1 | 3/2010 |

OTHER PUBLICATIONS

Häglund et al. "Dissolution Controlled Drug Release from Agarose Beads" Drug Development and Industrial Pharmacy, vol. 20, 1994—Issue 6, abstract (Year: 1994).*
"A core gut microbiome in obese and lean twins"; Peter J. Turnbaugh et al.; Nature; vol. 457, Jan. 22, 2009; (6 pages).
"The Macrophage Mannose Receptor Induces IL-17 in Response to Candida Albicans"; Frank L. van de Veerdonk; Cell Host & Microbe; 2009-02-006; (12 pages).
"Environmental pH modulation by pathogenic fungi as a strategy to conquer the host"; Slavena Vylkova; PLOS Pathogens; Feb. 27, 2017; (6 pages).
"Characterization of yeasts colonizing in healthy individuals"; YL Yang et al.; Medical Mycology; Jan. 2011; 49; 103-106.
"Focuses specificity of intestinal Th17 cells towards commensal bacterial antigens"; Yi Yang et al.: Nature; vol. 510; Jun. 5, 2014.
"Thermotolerance and the Heat-shock Response in Candida Albicans"; Marie Zeuthen et al.; Journal of General Microbiology; 1989; 135; pp. 2509-2518.
"Changing Epidemiology of Classical and Emerging Human Fungal Infections: A Review"; Khaled H. Abu-Elteen et al.; Jordan Journal of Biological Sciences; vol. 5, No. 4, Dec. 2012 (16 pages).
"Role of Yeast Cell Growth Temperature on Candida Albicans Virulence in Mice"; Penny P. Antley et al.; Infection and Immunity; Nov. 1988; (7 pages).
"Cell Human Anti-fungal Th17 Immunity and Pathology Rely on Cross-Reactivity against Candida Albicans"; Petra Bacher et al; Mar. 7, 2019 (32 pages).
"The gut microbiota as an environmental factor that regulates fat storage"; Fredrik Backhed et al.; www.pnas.org/cgi/dio/10.1073/pnas.0407076101; Nov. 2, 2004 (6 pages).
"The glutamate/GABA-glutamine cycle" aspects of transport, neurotransmitter homeostasis and ammonia transfer; Lasse K. Bak et al.; Journal of Neurochemistry, 2006, 98 (13 pages).
"Multidrug-Resistant Candida Haemulonii and C. Auris, Tel Aviv, Israel"; Ronen Ben-Ami et al.; Emerging Infectious Diseases—www.cdc.gov/eid, vol. 23, No. 2, Feb. 2017 (9 pages).
Anaerobic Growth of Candida Albicans Does Not Support Biofilm Formation Under Similar Conditions Used for Aerobic Biofilm; Swarajit K. Biswas et al.; Current Microbioloty; Department of Microbiology and Immunology, Texas Tech University Health Sciences Center, Jan. 5, 2005; (5 pages).
"HIV-Protease Inhibitors Reduce Cell Adherence of Candida Albicans Strains by Inhibition of Yeast Secreted Aspartic Proteases"; Margarete Borg-Von Zepelin et al.; The Society for Investigative Dermatology, Inc., vol. 113, No. 5, Nov. 1999; (5 pages).
"Mannose-Binding Lectin (MBL) Facilitates Opsonophagocytosis of Yeasts but Not of Bacterial Despite MBL Binding"; Nannette Brouwer, et al.; The Journal of Immunology; Aug. 1, 2018; (10 pages).
Immune Recognition "A new receptor for B-glucans"; Nature, vol. 413, Sep. 6, 2001; www.nature.com; Gordon D. Brown et al.; (2 pages).
"Dectin-1 is a major B-Glucan Receptor on Macrophages"; Gordon D. Brown et al.; J. Exp. Med.; vol. 196, No. 3, Aug. 5, 2002; (6 pages).

(Continued)

*Primary Examiner* — Ruth A Davis
(74) *Attorney, Agent, or Firm* — Lanier Ford Shaver & Payne PC; Gerald M. Walsh

(57) ABSTRACT

An anti-inflammatory composition of *Candida albicans* which comprises heat-killed *Candida albicans* in combination with a neuroprotective supplement. The composition provides a method of stimulating a host immune response capable of reducing a total *Candida albicans* yeast load below the threshold necessary for the host to keep the *Candida albicans* yeast and related yeast species in a commensal, non-invasive state. This effect inhibits or prevents chronic inflammation related to invasive *Candida* genus and allows the composition to be useful for the prevention, prophylaxis, and/or treatment of chronic inflammatory conditions, as well as diseases and disorders of the central nervous system resulting from high L-glutamate levels due to *Candida albicans* in the gastrointestinal system.

19 Claims, No Drawings

(56) References Cited

OTHER PUBLICATIONS

"Dendritic Cell Interaction with Candida Albicans Critically Depends on N-Linked Mannan"; Alessandra Cambi et al.; The Journal of Biological Chemistry, vol. 283, No. 29, pp. 20590-20599; Jul. 18, 2008.
"Effectiveness of a Vaccine Composed of Heat-Killed Candida Albicans and a Novel Mucosal Adjuvant, LT (R192G), against Systemic Candidiasis"; Lucia Cardenas-Freytag et al.; Infection and Immunity, Feb. 1999; vol. 67, No. 2; pp. 826-833.
"Interplay between Candida Albicans and the Mammalian Innate Host Defense"; Shih-Chin Cheng et al.; Journals. ASM.org; Infection and Immunity, pp. 1304-1313; Apr. 2012; vol. 80, No. 4.
"Protection Against Experimental Aspergillosis by heat-killed yeast is not antibody dependent"; Karl V. Clemons et al.; Medical Mycology, 2014, 52, pp. 422-426.
"Evidence for Degradation of Gastrointestinal Mucin by Candida Albicans Secretory Aspartyl Proteinase"; Ana-Rosa Colina et al.; Infection and Immunity, Nov. 1996, p. 4514-4519.
"Synergistic Combinations of Antifungal and anti-virulence agents to fight against Candida Albicans"; Jinhui Cui et al.; Virulence 6:4; pp. 362-371; May/Jun. 2015.
"Human Gut Bacteroidetes can utilize yeast mannan through a selfish mechanism"; Fiona Cuskin et al.; Nature, Jan. 8, 2015; (38 pages).
"Characterizatioin of Binding of Candida Albicans to Small Intestinal Mucin and its Role in Adherence to Mucosal Epithelial Cells"; Louis de Repentigny et al.; Infection and Immunity, Jun. 2000, pp. 3172-3179; vol. 68, No. 6.
"Flow Cytometry and Cell Sorting for Yeast Viability Assessment and Cell Selection"; Daniel Deere et al.; Yeast, vol. 14, pp. 147-160; (1998).
"Deficient Beta-Mannosylation of Candida Albicans Phospholipomannan Affects the Proinflammatory Response in Macrophages"; Audrey Devillers et al.; PLOS ONE, www.plosone.org; Dec. 2013; vol. 8, Issue 12 (11 pages).
"Activation of HIF-1x and LL-37 by commensal bacteria inhibits Candida Albicans colonization"; Di Fan et al.; Nature Medicine; vol. 21; No. 7; Jul. 2015.
"Review Article: Bacterial translocation in the critically ill—evidence and methods of prevention"; M. Gatt et al.; Alimentary Pharmacology & Therapeutics; pp. 741-757; 2007.
"Metagenomic Analysis of the Human Distal Gut Microbiome"; Steven R. Gill et al.; NIH Public Access, Science; Jun. 2, 2006; (12 pages).
"Characterisation of a refined rat model of respiratory infection with Pseudomonas Aeruginosa and the effect of ciprofloxacin"; E. J. Growcott et al.; Journal of Cystic Fibrosis; 2011; pp. 166-174.
"Genetic Drivers of Multidrug Resistance in Candida Glabrata"; Kelley R. Healey et al.; Frontiers in Microbiology; Public Health Research Institute; Dec. 15, 2016; (9 pages).
Human Corneal Epithelial Cells Produce Antimicrobial Peptides LL-37 and B-Defensins in Response to Heat-Killed Candida Albicans; Xia Hua et al.; Ophthalmic Res. 2014; 51(4); pp. 179-186.
"Physiological Actions of Taurine"; R. J. Huxtable; Physiological Review; vol. 72; No. 1; Jan. 1992.
"Flavonoid nutraceuticals and ionotropic receptors for the inhibitory neurotransmitter GABA"; Graham A.R. Johnston; Pharmacology, School of Medicine; Neurochemistry International 89 (2015); pp. 120-125.
Specific Recognition of Candida Albicans by Macrophages Requires Galectin-3 to Discriminate *Saccharomyces cerevisiae* and Needs Association with TLR2 for Signaling; Thierry Jouault, et al.; The Journal of Immunology; 2006; 177; pp. 4679-4687.

"Probiotics microbes: do they need to be alive to be beneficial?"; Jasmeet Kataria et al.; Emerging Science; Nutritional Review; 2009; vol. 67; pp. 546-550.
Presynaptic, extrasynaptic and axonal GABAa Receptors in the CNS: where and why?; Dimitri M. Kullmann et al.; Progress in Biophysics and Molecular Biology; 87 (2005); pp. 33-46.
Live and Heat-Killed Lactobacillus rhammosus GG: Effects on Proinflammatory and Anti-Inflammatory Cytokines/Chemokines in Gastrostomy-Fed Infant Rats; Nan Li et al.; Pediatric Research; vol. 66, No. 2, 2009 (5 pages).
Global and regional burden of disease and risk factors, 2001: Systematic Analysis of Population Health Data: Alan D. Lopez et al.; www.thelancet.com; vol. 367; May 27, 2006; (11 pages).
"Control of Dimorphism in a Biochemical Variant of Candida Albicans"; D. Mardon et al.; Journal of Bacteriology; Nov. 1969; pp. 701-707.
"Anti-HIV-1 Activity, protease inhibition and safety profile of extracts prepared from Rhus parviflora"; Manoj Modi et al.; BMC Complementary and Alternative Medicine; 2013, 13:158.
"Candidalysis is a fungal peptide toxin critical for mucosal infection"; David L. Moyes et al.: Nature, Apr. 7, 2016; 532; (42 pages).
"Candida Albicans Yeast, Pseudohyphal, and Hyphal Morphogenesis Differentially Affects Immune Recognition"; Liliane Mukaremera et al.; Frontiers in Immunology; Jun. 7, 2017 (12 pages).
"Immune sensing of Candida Albicans Requires Cooperative Recognition of mannans and glucans by lectin and Toll-like receptors"; Mihai G. Netea et al.; The Journal of Clinical Investigation; vol. 116, No. 6; Jun. 2006.
Candida Albicans Infection of Caenorhabditis Elegans Induces Antifungal Immune Defenses; Read Pukkila-Worley et al.; PLOS Pathogens; Jun. 2011; vol. 7, Issue 6 (13 pages).
"Biological Activities of Extracts from Sumac (*Rhus* spp.): a Review"; Sierra Rayne et al.; Plant Foods Hum Nutr; 2007; 62:165-175.
"Dectin-2 Recognition of x-Mannans and Induction of TH17 Cell Differentiation is Essential for Host Defense Against Candida Albicans"; Shinobu Saijo et al.; Immunity 32; 681-691; May 28, 2010.
"GABA-Modulating Phytomedicines for Anxiety: a Systematic review of preclinical and clinical evidence"; Karen Savage et al.; Wiley, Jul. 17, 2017; (16 pages).
"Taurine-induced long-lasting enhancement of synaptic transmission in mice: role of transporters"; O.A. Sergeeva et al.; J Physiol (2003) 550, pp. 911-919.
"Rhus parviflora and its biflavonoid constituent, rhusflavone, induced sleep through the positive allosteric modulation of GABAa-benzodiazepine receptors"; Sabina Shrestha et al.; Journal of Ethnopharmacology 142 (2012); 213-220 pages.
"Bile Acids and Metabolic Regulation"; Bart Staels et al.; Diabetes Care, vol. 32, Supplement 2; Nov. 2009 (9 pages).
"The Effects of Benzodiazepines on Cognition"; Stewart, S.; J Clin Psychiatry 2005; 66 (suppl. 2); (5 pages).
"*Saccharomyces cerevisiae*- and Candida Albicans-Derived Mannan Induced Production of Tumor Necrosis Factor Alpha by Human Monocytes in a CD14 and Toll-Like Receptor 4-Dependent Manner"; Hiroyuki Tada et al.; Microbiol. Immunol; 46(7); 503-512, 2002.
"A Bacteroidetes locus dedicated to fungal 1, 6-B-glucan degradation: Unique substrate conformation drives specificity of the key endo-1, 6-B-glucanase"; Max J. Temple et al.; ASBMB; J. Biol. Chem (2017) 292—10639-10650.
"An obesity-associated gut microbiome with increased capacity for energy harvest"; Peter J. Turnbaugh et al.; Nature; vol. 444, Dec. 21/28, 2006; (5 pages).

\* cited by examiner

COMPOSITION OF HEAT-KILLED YEAST AND TAURINE OR A PHYTOMEDICINE FOR THE TREATMENT OF CHRONIC INFLAMMATION

FIELD OF THE INVENTION

This invention relates to a novel formulation of killed yeast, specifically *Candida*, combined with taurine or a phytomedicine, its use for immunoprophylaxis and the treatment of chronic inflammation in human and veterinary medicine as well as methods for its preparation.

BACKGROUND OF THE INVENTION

It is known that the standard western diet leads to obesity and chronic, low-grade inflammation and inflammatory diseases, such as type 2 diabetes myelitis, cardiovascular disease, cancer, and more (Lopez, 2001). By definition, "chronic" describes a state of persistence that occurs for a long time. Chronic inflammatory diseases are characterized by long-term dysfunction leading to an inflammatory state in the body. It appears that a root cause of chronic inflammation is an unchanging or persisting stimulus of inflammation. Agents that cause an inflammatory response are ones that are not recognized as "self" by the host immune system. In autoimmunity, it has been hypothesized that some dysfunction of the immune system allows it to erroneously recognize self as non-self and mount an immune response. However, it is plausible that the immune system is responding properly, not to self, but to a persistent pathogen that is continuously triggering an inflammatory response. This chronic inflammatory state could result in system-wide disorders and diseases, including cancers, if left untreated.

The human GI tract includes all three kingdoms of commensal microbes reaching the highest density of $10^{14}$ cells/g in the colon (Gill, 2006). A high Firmicutes/Bacteroidetes (FIR/BAC) phylum ratio is a known marker for obesity (Turnbaugh, 2006 & 2009, Backhed, 2004). Certain taxa within the Bacteroidetes phylum digest mannan glycoproteins & beta-glycans found in the outer layer of a yeast cell wall (Cuskin, 2015 & Temple, 2017). It is expected that a sufficiently large population of yeast-consuming taxa present in the gut milieu results in more exposure of yeast beta-glucans to the host immune system. Exposed beta-glucans initiate both an innate and adaptive immune response against yeast cell components and result in a greater clearance of the yeast population present. In fact, studies show that mice fed a standard laboratory mouse diet resist colonization by *Candida albicans* (CA) due to the increased presence of Bacteroidetes and Clostridial Firmicutes in the murine intestine (Fan, 2015). This observation indicates that a low FIR/BAC ratio of bacterial taxa in the gut should result in a higher immune clearing of yeast cells and a lower population of yeast taxa. Conversely, a higher FIR/BAC ratio of bacterial taxa in the gut, as is seen in obesity, should result in lower immune clearing of yeast cells and a higher population of yeast taxa.

Similar to any ecosystem that includes decaying matter, the human gut microbiome contains a rich diversity of Eukaryotic fungal species at an approximate density of $10^6$ CFU/mL in the colon (Abu-Elteen, 2012). *Candida albicans* (CA) is a saprotrophic commensal, yet potentially invasive yeast species of the human gastrointestinal system, colonizing the gastrointestinal system of up to seventy percent of the Western population (Abu-Elteen, 2012). It is also a potent stimulator of the host inflammatory immune response (Jouault, 2006; Devillers, 2013; Netea, 2006; Tada, 2002; Brouwer, 2008; Brown, 2002; Saijo, 2010; Cambi, 2008). This yeast species possesses certain key virulence factors that have allowed it to even persist in the mucous membranes of an immune-competent host. The main virulence factor of CA is the ability to switch between yeast, pseudohyphal and hyphal forms (Mukaremera, 2017). The ability of CA to morph between three different forms differentially affects host immune recognition of this fungus. The hyphal form is key in the process of host epithelial barrier invasion. *Candida* is capable of attaching to and invading the mucous layer which lines the epithelial lumen of the gastrointestinal tract (de Repentigny, 2000; Yang, 2011). In the hyphal form, CA is able to degrade gastrointestinal mucins using fungal secretory aspartyl proteinase (Sap2p) (Colina, 1996). Candidalysin is a cytolytic peptide toxin found in CA which is able to disrupt the host epithelial barrier, damage cells and modulate the host immune response (Moyes, 2016). Additionally, intestinal barrier damage/dysfunction allows the translocation of intestinal microbes and their products and toxins into the blood and tissues surrounding the intestines. This bacterial translocation contributes to the development of systemic inflammation in the host (Gatt, 2007).

During fungal hyphal invasion, host epithelial cells respond with antimicrobial peptides, pro-inflammatory cytokines and chemokines (Cheng, 2012). Dectin-2 recognition of CA yeast alpha-mannans induces IL-1-beta & IL-23 secretion which induces immune CD4+ Th17 cell differentiation, a key step in the inflammatory process (Saijo, 2010). Binding of either Dectin-1 or Dectin-2 to the yeast substrate induces the release of immune-modulatory cytokines which activate the innate immune response (Brown, 2001). Current research has shown that CA is the major fungal inducer of immune Th17 cells (Bacher, 2019). Intestinal Th17 cells have been shown to be antigen specific (Yang, 2014). It is expected that if fungal breaching of the gut epithelial barrier is a persistent event, a state of chronic systemic inflammation occurs.

Killing any invasive species of yeast in the mucosal membrane is not expected to be useful in preventing chronic inflammation. Yeasts, including *Candida* species, are saprotrophs in the gut ecosystem. They help to digest decaying organic matter, releasing nutrients that are beneficial to the entire commensal community, as well as to the host. To completely remove yeast from the gut ecosystem would potentially throw the gut into a state of dysbiosis that would shift the growth of multiple taxa in the system, possibly even leading to the death of the host. In addition, *Candida albicans* has proven to be almost impossible to eliminate. CA growth cannot be altered by a change in environmental pH, since it has evolved mechanisms to modulate environmental pH by producing acids to cause acidification or alkalinization of tissues, through the release of ammonia molecules (Vylkova, 2017). CA cannot be eliminated through pharmacological means, since many drug-resistant genomic variants of CA and other *Candida* species have now been identified in patient samples (Cui, 2015; Healey, 2016; Ben-ami, 2017). Finally, CA has evolved mechanisms to block every potential immune attack, making it a well-adapted persistent pathogen (Cheng, 2012; Cui, 2015).

It has been shown in previous studies that heat-killed (HK), ultraviolet-inactivated or components of probiotic species may be just as effective as live cells when administered orally (Kataria, 2009; Li, 2009).

Heat-killed yeast contains "yeast extract," a substance rich in glutamate (L-glutamic acid, L-glutamate). Glutamate is an excitatory neurotransmitter and essential amino acid for brain metabolism and function. Addition of this substance to the diet would increase dietary glutamate levels in the gut, and potentially, the brain. This has positive and negative consequences, in vivo. In 1969, it was reported by Mardon, et al. that CA dimorphic changes can be controlled through changes in the carbon dioxide to oxygen ratio and addition of certain amino acid nitrogen sources, such as L-glutamic acid and L-glutamine (Mardon, 1969). The addition of amino acids such as L-glutamic acid and L-glutamine as the sole nitrogen source with or without changes to the carbon dioxide:oxygen ratio kept CA in the yeast (non-invasive) form. This would be a positive result in the context of the intestinal, mucosal environment as it would keep CA in the yeast form, preventing the switch to hyphal form and reducing epithelial invasion. However, the amino acid L-glutamate (or L-glutamic acid) is an excitatory neurotransmitter acting on neurons of the central nervous system. High levels of glutamate have been implicated in neuronal hyperexcitability, as is seen in seizure disorders, chronic anxiety, chronic stress, posttraumatic stress disorder and other diseases. As a result of the high glutamate content in heat-killed yeast, the use of heat-killed yeast to treat inflammation heretofore has not been practical or feasible.

SUMMARY OF THE INVENTION

The anti-inflammatory composition of *Candida albicans* of this invention comprises heat-killed yeast, specifically *Candida albicans*, in combination with a neuroprotective supplement. The neuroprotective supplement is, preferably, taurine or a positive allosteric modulator of the GABA-A receptor, or a combination thereof. The positive allosteric modulator is, preferably, a phytomedicine (whole-plant or plant-extract compound), selected from the polyacetylenic alcohol, terpenoid, and flavonoid groups (consisting of, but not limited to, kava, valerian, pennywort, hops, chamomile, ginkgo biloba, passionflower, ashwagandha, skullcap, lemon balm, sumac of the *Rhus* genus), or combinations thereof. The sumac of the *Rhus* genus is, preferably, *Rhus parviflora* Roxb. The heat-killed yeast comprises heat-killed *Candida* genus or other yeast species, and cellular debris in a powder form. The powder form may be impregnated into agarose resin beads or bound to a chitin-coated substrate for a controlled release formulations and method of administration.

This invention provides a method of treatment or prophylaxis of chronic inflammation related to invasive yeast. The method comprises administering to a subject in need thereof an effective amount of an anti-inflammatory preparation of heat-killed yeast, comprising heat-killed *Candida* genus or other yeast species and a neuroprotective supplement. This anti-inflammatory preparation is administered to the subject, preferably, by the oral, enteral, or vaginal route of administration. The heat-killed yeast and the neuroprotective supplement can also be administered separately sequentially.

The effective amount is the amount sufficient to stimulate an immune response in the subject capable of reducing the total *Candida albicans* yeast, and related yeast species load below a threshold necessary for the subject to keep the *Candida albicans* yeast and related yeast species in a commensal, non-invasive state.

An advantage of the present invention is a heat-killed yeast preparation that is useful for the prevention and/or treatment of invasive *Candida* genus and related yeast species. This preparation is appropriate for the prevention, prophylaxis, and/or treatment of any and all chronic inflammatory conditions of a mammalian host, to include, but not limited to, obesity, cardiovascular disease, Type I and II diabetes mellitus, cancer, high blood pressure, all gastrointestinal illnesses to include Chron's, colitis, and inflammatory bowel syndrome, inflammatory bowel disease, reproductive infertility disorders, hormonal imbalances, all mental health disorders to include addictions, all autism spectrum disorders to include attention deficit hyperactivity disorder, all autoimmune disorders, fibromyalgia, myalgic encephalomyelitis/chronic fatigue syndrome, all allergies, atopic dermatitis, sleep disorders, candidiasis/thrush/yeast infections, and amelioration of drug side effects. This preparation could be used to treat any invasive fungal infection. Additionally, this preparation could be used to prevent the dissemination of certain protease-dependent viruses such as HIV-1 and/or HIV-2.

DETAILED DESCRIPTION OF THE INVENTION

While the following description details the preferred embodiments of the present invention, it is to be understood that the invention is not limited in its application to the details described herein, since the invention is capable of other embodiments and of being practiced in various ways.

The possibility was considered that introduction of heat-killed yeast, specifically, *Candida albicans* (HKCA) to the gut microbiome might increase all microbial taxa with the ability to consume yeast cell components, resulting in the reduction of total live yeast cells. The possibility was also considered that heat-killed yeast, specifically *Candida*, within the gut milieu might stimulate both an innate and adaptive immune response that results in greater phagocytosis of yeast cells and cell components as well as antibodies specific for every portion of the CA yeast cell. The greater phagocytosis of yeast cells might then reverse chronic inflammation in a subject whose elevated *Candida albicans* was sustaining the chronic inflammation.

The oral, enteral or vaginal administration of inactivated heat-killed yeast, specifically *Candida*, of this invention stimulates a host immune response capable of reducing the total CA yeast load below the threshold necessary for the host to keep the CA yeast and related yeast species in a commensal, non-invasive state. The invention further provides a formulation of heat-killed yeast, specifically *Candida*, that includes a neuroprotective supplement that protects against excessive, neurotoxic extracellular or intracellular levels of glutamate. The neuroprotective supplement may be taurine (2-aminoethane sulfonic acid) or a positive allosteric modulator (PAM) of the gamma-aminobutyric acid (GABA)-A receptor. The heat-killed yeast formulation provides a means for the prevention, prophylaxis, inhibition, and/or treatment of invasive *Candida* genus and related yeast species in subjects such as mammals, including humans.

GABA is an amino acid that acts as the principle inhibitory neurotransmitter in the central nervous system (CNS). Production of GABA is the result of the enzymatic breakdown of the precursor molecules, glutamine and glutamate (Bak, 2006). This enzymatic reaction uses taurine, vitamin B6 and magnesium as co-factors for glutamate decarboxylase (GAD). GABA receptors are found in every region of the human brain. When activated, the GABA-A receptor works to hyperpolarize the neuron and reduces the likelihood of an action potential (Kullman, 2005). A delicate balance between the excitatory neurotransmitter, glutamate, and the inhibitory neurotransmitter, GABA in the CNS is essential for the vitality, health and even life of many species, including humans.

Taurine is an abundant amino acid and neurochemical that is involved in bioacid synthesis, the regulation of osmolarity, ion channel activity, neuronal growth and metabolism (Chepkova, 2002; Chepkova, 2006; Huxtable, 1992; Sergeeva, 2003). Taurine is conjugated to bile acids and recycled when primary bile acids are changed to secondary bile acids by certain phyla of bacteria in the gut of certain mammals (Staels, 2009). Biological actions of taurine include, but are not limited to, hypotensive action, antiarrhythmic, retardation of lesion development in calcium overload, anticonvulsant, maintenance of cerebellar function, thermoregulation, resistance to anoxia/hypoxia, altered learning, and anti-tremor actions (Huxtable, 1992).

Enhancement of the GABA-A receptor function can be accomplished with synthetic pharmacologic drugs such as benzodiazepines, semi-synthetic opioids, or natural, plant-based PAM phytomedicines, such as the flavonoid nutraceuticals (Savage, 2017). GABA-modulating PAM phytomedicines include, but are not limited to, kava, valerian, pennywort, hops, chamomile, Ginkgo biloba, passionflower, ashwagandha, skullcap and lemon balm (Savage, 2017). In addition to this list, edible sumac of the *Rhus* genus are used therapeutically in neurological disorders, diabetes mellitus, cancer, stroke, inflammation, diarrhea, rectal and intestinal cancer, oral diseases and more (Abu-Reida, 2014; Djakpo, 2010; Shrestha, 2012).

Benzodiazepines target the GABA-A receptor and enhance the GABA-mediated inhibition of neuron excitability (Kullman, 2005). Benzodiazepine drugs only provide modest benefits, since a substantial number of patients report insufficient alleviation of anxiety symptoms. Additionally, benzodiazepines are noted for negative side effects such as depressed concentration, memory impairment, tolerance and an addictive quality (Stewart, 2005). Natural PAM phytomedicines fall into three categories including polyacetylenic alcohols, terpenoids, and flavonoids, all of which are hypothesized to interact at the GABA-A allosteric sites. In particular, flavonoids are well-known to positively modulate the GABA-A receptor (Johnston, 2015).

One flavonoid that is an especially potent modulator of the GABA-A receptor is the Nepalese sumac, *Rhus parviflora* Roxb. (Anacardiaceae). The leaves and fruit of this plant have been shown to be therapeutic for anxiety, insomnia, epilepsy, rheumatoid arthritis (Shrestha, 2012). In traditional Ayurvedic medicine, this plant species is used to treat neurological complications and stomach disorders. The biflavones agathisflavone and amentoflavone of *Rhus parviflora* both exhibit good affinity for the GABA-A receptor (Shrestha, 2012). Medicinally, the *Rhus* spp. is used as an antifibrogenic, antifungal, anti-inflammatory, antimalarial, antimicrobial, antimutagenic, antioxidant, antithrombin, antitumorigenic, antiviral, cytotoxic, hypoglycaemic and leukopenic (Rayne 2007). *Rhus parviflora* has been shown to exert anti-HIV-1 activity due to protease inhibition (Modi, 2013). Interestingly, HIV-1 protease inhibitors are able to reduce epithelial cell adherence by *Candida albicans* due to the inhibition of the yeast secreted aspartic proteases (Borg-von Zepelin 1999). Moreover, *Rhus parviflora* has been shown to have no adverse effects on epithelial cell lining or the viability of lactobacilli species. It also shows no significant increase in pro-inflammatory cytokines in human vaginal epithelial cells (Modi, 2013). For these reasons, and more, the combination of HKCA/*Rhus parviflora* supplement could be used as an antifungal/antiviral/antibacterial preventative or therapeutic for HIV-1 infection as well as other viral or bacterial sexually transmitted diseases (STDs).

The heat-killed yeast, specifically *Candida*, can be provided as a supplement, probiotic, food item, beverage item or suppository containing the heat-killed yeast, specifically *Candida*, both the soluble & insoluble components, or any fraction thereof, combined with taurine or a synthetic, semi-synthetic or natural PAM phytomedicine. The heat-killed yeast can be used for oral, enteral (gastrointestinal system), or vaginal administration in any mammal, including humans of any age or sex, with the possible exception of pregnant females. Oral administration of heat-killed yeast, specifically *Candida*, coupled with taurine and/or a natural PAM phytomedicine provides a potent and safe therapeutic limitation of the growth of CA. This combination harnesses the aid of certain microbial taxa within the gut to prevent the invasion of this yeast genus, resulting in a reduction of chronic inflammation. This reduction in chronic inflammation is expected to prevent diseases and disorders, including diabetes mellitus, cardiovascular disease and cancers that result from the chronic inflammation. Additionally, heat-killed yeast, specifically *Candida*, coupled with taurine or a natural PAM phytomedicine can be applied to mental health disorders such as depression, anxiety, attention deficit conditions, Autism and spectrum disorders, epilepsy, Parkinson's disease, opioid addictions, chronic fatigue syndrome, and various other mental health disorders.

Preparation of Heat-Killed Yeast, Specifically *Candida*, Anti-Inflammatory Composition A wild-type strain of *Candida albicans* or other yeast species, is grown to achieve sustained exponential growth in Yeast nitrogen base (YNB) broth medium supplemented with 50 mM dextrose, for 12-24 hours within a temperature range of 23-37 degrees Celsius with shaking at approximately 180 rpm (Biswas, 2005; Antley, 1988). Yeast cells are washed by centrifugation with phosphate-buffered saline (PBS, pH 7) multiple times and the yeast suspension adjusted to approximately $1 \times 10^8$ cells/mL. Cells and cell fragments are disrupted by sonication of the cell suspension. Since CA lethal temperature has been found to be 55 degrees Celsius, yeast is killed/inactivated by heating the suspension at 70 degrees Celsius for approximately three hours or 100 degrees Celsius for approximately one hour (Zeuthen, 1989). The absence of yeast cell viability is checked by methods such as flow cytometric assessment and growth on nutrient agar (Hernlem, 2010; Deere, 1998). The yeast cell suspension is dried to form a powder.

Heat-killed yeast/taurine (2-aminoethane sulfonic acid) or heat-killed yeast/PAM phytomedicine, either in powder form or bound to agarose beads or a chitin matrix, can be encased by an enteric-coated capsule. As a food or beverage item, heat-killed yeast/taurine or PAM phytomedicine can be in powder form and added to the food or beverage product. As a suppository, heat-killed yeast/taurine or PAM phytomedicine can be in powder form and added to the base material (cocoa butter, polyethylene glycol, hydrogel, etc.) of the suppository.

Heat-killed yeast cells and cellular debris in the powder form can additionally be impregnated into agarose resin beads or bound to a chitin-coated substrate for a controlled-release formulation and method of administration (Growcott, 2011). Additional probiotic strains or supplements could be combined within the defined matrix.

Test for In-Vivo Anti-Inflammatory Efficacy of Heat-Killed Yeast, Specifically *Candida*

The efficacy of the heat-killed yeast anti-inflammatory composition can be demonstrated in a gnotobiotic mouse model. 20 gnotobiotic mice are given a human fecal microbiota transfer (FMT) by anal route at approximately three months of age from an individual that is of an obese phenotype, colonized by *Candida albicans* and exhibiting symptoms of chronic inflammation, related to the presence of *Candida albicans*. Human fecal samples used for the -FMT are screened by 16SrRNA and 18SrRNA in order to verify bacterial and fungal intestinal commensal organisms. The mice are housed in a specific, microbe-controlled environment at room temperature and fed a controlled murine chow, containing standard amounts of protein, fat, vitamins/minerals and carbohydrates, yet void of any probiotic strains, including yeast.

At approximately five months of age, one half of the mice (Group 1) receive a therapeutic dose of the heat-killed yeast anti-inflammatory composition by the oral route, dispensed within the murine chow at a dose of 10 mg/kg/day. The other half of the mice (Group 2) receive microcrystalline cellulose 10 mg/kg/day by the oral route, dispensed within the food, and serve as a control group. Dosing is continued in each group for the remainder of the experiment. Body composition/BMI and weight are assessed for each animal at the initiation of the experiment, after the FMT, at the start of therapy, and at one-month intervals after therapy begins for a total of six months. Fecal material is collected at the start and at each interval and assessed by 16SrRNA sequence and 18SrRNA for bacterial and fungal composition. Serum is collected at the start, one week after fecal transfer, at the start of therapy, one month after therapy, and at the last time point of therapy. Serum biomarkers of inflammation are analyzed for each sample.

The fecal transfer causes the mice to develop an inflammatory-related weight gain, associated with increased serum inflammatory biomarkers, increased fungal population (*Candida* genus), increased Firmicutes, and decreased Bacteroidetes phylum within fecal samples. These changes produced by the fecal transfer are reduced 70% to 90% in the Group 1 mice, with statistical significance. The oral administration of the heat-killed yeast anti-inflammatory composition is shown by this test to have anti-inflammatory efficacy on chronic inflammation in vivo. Group 1 mice are also shown to have normal motor coordination and behavioral characteristics with no observable toxicity.

The preferred embodiments of this invention include an anti-inflammatory composition or preparation of heat-killed yeast, specifically *Candida albicans*, comprising heat-killed yeast plus a neuroprotective supplement. The neuro protective supplement is, preferably, taurine or one or more positive allosteric modulators of the GABA-A receptor or a combination thereof. The preferred positive allosteric modulators are phytomedicines as disclosed above. The oral dose of the heat-killed yeast composition is 0.05 g to 3 g, preferably 1.5 g to 3 g, per day. The dose of taurine in the heat-killed yeast composition is 40 to 3,000 mg per day. The dose of the positive allosteric modulator is 10 to 3,000 mg per day. The heat-killed yeast and neuroprotective supplement may be administered simultaneously or sequentially.

The heat-killed yeast powder plus taurine and/or one or more positive allosteric modulators of the GABA-A receptor can be formulated by a person of ordinary skill in the art in oral, enteral, and vaginal dosage forms using methods well known in the art. Dosage forms of the invention comprise capsules, tablets, lozenges, syrups, oral Suspensions, oral emulsions, pills, and vaginal Suppositories, Excipients used according to the invention comprise, for example, diluents, carriers, vehicles, preservatives, colorants, disintegrants, binding agents, emulsifying agents, solubilizing agents, netting agents, solvents, buffering agents, gel-forming agents, thickening agents, antioxidants as well as flavor and odor correctives.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. It will be understood that various changes in the details, materials, and arrangements of the parts which have been described and explained above in order to explain the nature of this invention may be made by those skilled in the art without departing from the principle and scope of the invention as recited in the following claims.

We claim:

1. A method of treatment or prophylaxis of chronic inflammation due to invasive *Candida* genus, comprising administering to a subject an effective amount of an anti-inflammatory preparation of heat-killed yeast comprising heat-killed *Candida* or other species of heat-killed yeast and a neuroprotective supplement stimulating an immune response in the subject with the effective amount reducing, with the immune response, a total yeast load in the subject below a threshold necessary for the subject to keep the yeast load in a commensal, non-invasive state; and increasing the production of gamma-aminobutyric acid (GABA) and/or enhancing GABA-A receptor function in the subject with the neuroprotective supplement and thereby protecting the subject against neurotoxic levels of glutamate present in the anti-inflammatory preparation of heat-killed yeast.

2. The method of claim 1, wherein administering is by the oral, enteral, or vaginal route of administration, wherein administration by the oral route in humans is in the amount of 0.05 to 3 grams of the anti-inflammatory preparation of heat-killed yeast.

3. The method of claim 1, wherein the anti-inflammatory preparation of heat-killed yeast and the neuroprotective supplement are administered simultaneously or sequentially.

4. The method of claim 1, further comprising suppressing the development of chronic inflammation in the subject, wherein the chronic inflammation is due to *Candida albicans*.

5. The method of claim 1, wherein the neuroprotective supplement is taurine or a positive allosteric modulator of the GABA-A receptor, or a combination thereof and wherein administration by the oral route in humans for taurine is in the amount of 40-3000 mg per day and for the positive allosteric modulator is in the amount of 10 to 3000 mg per day.

6. The method of claim 5, wherein the positive allosteric modulator is a phytomedicine.

7. The method of claim 6, wherein the phytomedicine is selected from a groups consisting of kava, valerian, pennywort, hops, chamomile, ginkgo biloba, passionflower, ashwagandha, skullcap, lemon balm, sumac of the genus *Rhus parviflora* Roxb, and combinations thereof.

8. The method of claim 5, further comprising limiting the growth of *Candida albicans* by administration by the oral route of the anti-inflammatory preparation of heat-killed yeast coupled with taurine and/or the positive allosteric modulator of the GABA-A receptor.

9. The method of claim 5, wherein the anti-inflammatory preparation of heat-killed yeast is administered in a food or beverage or both.

10. The method of claim 1, wherein the heat-killed yeast comprises heat-killed *Candida* or other species of heat-killed yeast cells and cellular debris in a powder form.

11. The method of claim 10, wherein the powder form is impregnated into agarose resin beads or bound to a chitin-coated substrate for a controlled release formulation and method of administration.

12. A method of treatment or prophylaxis of chronic inflammation due to invasive *Candida* genus, comprising administering to a subject an effective amount of an anti-inflammatory preparation of heat-killed yeast comprising heat-killed *Candida* or other species of yeast and a neuroprotective supplement, wherein administering is by the oral, enteral, or vaginal route of administration and wherein administration by the oral route in humans is in the amount of 0.5 to 3 grams of the anti-inflammatory preparation of heat-killed yeast wherein heat killed yeast stimulating an immune response in the subject with the effective amount reducing, with the immune response, a total yeast load in the subject below a threshold necessary for the subject to keep the yeast load in a commensal, non-invasive state; and increasing the production of gamma-aminobutyric acid (GABA) and/or enhancing GABA receptor function in the subject with the neuroprotective supplement and thereby protecting the subject against neurotoxic levels of glutamate present in the anti-inflammatory preparation of heat-killed yeast.

13. The method of claim 12, wherein the neuroprotective supplement is taurine or a positive allosteric modulator of the GABA-A receptor, or a combination thereof and wherein administration by the oral route in humans for taurine is in the amount of 40-3000 mg per day and for the positive allosteric modulator is in the amount of 10 to 3000 mg per day.

14. The method of claim 13, wherein the positive allosteric modulator is a phytomedicine.

15. The method of claim 14, wherein the phytomedicine is selected from a groups consisting of kava, valerian, pennywort, hops, chamomile, ginkgo biloba, passionflower, ashwagandha, skullcap, lemon balm, sumac of the genus *Rhus parviflora* Roxb, and combinations thereof.

16. The method of claim 15, further comprising suppressing the development of chronic inflammation in the subject, wherein the chronic inflammation is due to *Candida albicans*.

17. The method of claim 13 wherein the anti-inflammatory preparation of heat-killed yeast is administered in a food or beverage or both.

18. The method of claim 12, wherein the heat-killed yeast comprises heat-killed *Candida* or other species of heat-killed yeast cells and cellular debris in a powder form.

19. The method of claim 18, wherein the powder form is impregnated into agarose resin beads or bound to a chitin-coated substrate for a controlled release formulation and method of administration.

\* \* \* \* \*